United States Patent [19]

Hoeffkes et al.

[11] Patent Number: 4,898,725

[45] Date of Patent: Feb. 6, 1990

[54] PREPARATIONS FOR WASHING OR RINSING HAIR CONTAINING DI- OR TRI-CARBOXYLIC ACIDS

[75] Inventors: Horst Hoeffkes, Duesseldorf-Hellerhof; Kurt Seidel, Duesseldorf; Karl Giede; Alfred Struve, both of Hilden; Bert Gruber, Duesseldorf, all of Fed. Rep. of Germany

[73] Assignee: Henkel Kommanditgesellschaft auf Aktien, Duesseldorf, Fed. Rep. of Germany

[21] Appl. No.: 248,344

[22] Filed: Sep. 20, 1988

Related U.S. Application Data

[63] Continuation of Ser. No. 822,368, Jan. 24, 1986, abandoned.

[30] Foreign Application Priority Data

Feb. 2, 1985 [DE] Fed. Rep. of Germany ....... 3503618

[51] Int. Cl.$^4$ ................... A61K 7/075; A61K 7/080; C11D 3/20
[52] U.S. Cl. ................................ 424/70; 252/174.19; 252/DIG. 13
[58] Field of Search ................. 252/174.19, DIG. 13; 424/70, 78

[56] References Cited

U.S. PATENT DOCUMENTS

| | | | |
|---|---|---|---|
| Re. 29,337 | 8/1977 | Ward | 252/174.19 X |
| 2,167,502 | 3/1939 | Frew | 424/70 |
| 2,188,882 | 1/1940 | Clocker | 260/405 |
| 2,192,907 | 3/1940 | Harris | 424/70 X |
| 2,744,130 | 5/1956 | Winberg | 260/482 |
| 3,472,840 | 10/1969 | Stone et al. | 260/231 |
| 3,598,865 | 8/1971 | Lew | 260/210 R |
| 3,632,559 | 1/1972 | Basel et al. | 260/78 SC |
| 3,753,968 | 8/1973 | Ward | 260/97.6 |
| 3,836,537 | 9/1974 | Boerwinkle et al. | 260/29.6 |
| 3,910,862 | 10/1975 | Barabas | 260/79.3 |
| 3,912,808 | 10/1975 | Sokol | 424/71 |
| 4,157,388 | 6/1979 | Christiansen | 424/70 |
| 4,240,450 | 12/1980 | Grollier et al. | 132/7 |
| 4,252,695 | 2/1981 | Homme et al. | 424/70 X |
| 4,698,065 | 10/1987 | Hoeffkes et al. | 8/406 |
| 4,752,467 | 6/1988 | Konrad et al. | 424/70 |
| 4,834,971 | 5/1989 | Klenk et al. | 424/70 |

FOREIGN PATENT DOCUMENTS

| | | |
|---|---|---|
| 56595 | 7/1982 | European Pat. Off. . |
| 116439 | 8/1984 | European Pat. Off. . |
| 188216 | 7/1986 | European Pat. Off. . |
| 196398 | 11/1984 | Japan ............................. 252/174.19 |
| 296412 | 11/1972 | United Kingdom . |
| 2063671 | 12/1983 | United Kingdom . |

OTHER PUBLICATIONS

Chemical Abstract: 97:98173 (equiv. to EP 56 595).
Chemical Abstract:88:158285y.
Chemical Abstract: 101:197935 (equiv. to EP 116 439).
JP-A 54/129135.
Chemical Abstract: 105:158609 (equiv. to EP 188216 and U.S. 4,698,065; the Journal of the American Oil Chemists Society 52, pp. 219–224.
Handbuch der Kosmetika & Riechstoffe, vol. III, 2nd Ed. (1973) Dr. A. Huthig, pp. 419–420.
J. Am. Chem. Soc. 68 (1946), pp. 1373–1376.
J. Am. Chem. Soc. 39 (1962) pp. 534–545; J. Am. Chem. Soc. 52 (1975) pp. 219–224.

*Primary Examiner*—Jose G. Dees
*Assistant Examiner*—Susan S. Rucker
*Attorney, Agent, or Firm*—Ernest G. Szoke; Wayne C. Jaeschke; Henry E. Millson, Jr.

[57] ABSTRACT

An aqueous or aqueous-alcoholic composition useful for washing or rinsing hair which contains a water-soluble ionic polymer and from about 0.1 to 20% by weight of a water soluble salt of a di- or tri-carboxylic acid containing from 6 to 44 carbon atoms. The ionic polymers may be cationic, anionic, amphoteric or zwitterionic. Preferred di- or tri-carboxylic acids are those in which two of the carboxyl groups are separated from one another by at least 3 carbon atoms. The composition further includes a quaternary ammonium compound as a preferred component. Hair rinses preferably contain as an additional ingredient from about 0.1 to 10% by weight of a water-insoluble cosmetic oil or fat component, while shampoos additionally contain from about 1 to 25% by weight of anionic, ampholytic, zwitter-ionic or nonionic surfactant.

12 Claims, No Drawings

PREPARATIONS FOR WASHING OR RINSING HAIR CONTAINING DI- OR TRI- CARBOXYLIC ACIDS

This application is a continuation of application Ser. No. 822,368, filed Jan. 24, 1986, now abandoned.

BACKGROUND OF THE INVENTION

1. Field of the Invention

This invention relates to aqueous or aqueous-alcoholic compositions containing water-soluble ionic polymers and water-soluble salts of di- or tri-carboxylic acids useful for washing or rinsing hair.

2. Description of Related Art

It is known that water-soluble ionic polymers can be added to hair-washing preparations not only to augment cleaning but also to improve cosmetic properties, particularly the combability or dressability and set of the hair. Cationic, anionic and amphoteric or zwitter-ionic polymers have been proposed as suitable ionic polymers for this purpose. Mixtures of cationic polymers and anionic polymers, mixtures of cationic and amphoteric polymers and mixtures of anionic and amphoteric polymers also have been proposed.

In a similar fashion, water-soluble ionic polymers also can be added to hair rinsing preparations, used after washing the hair with standard conditioner-free shampoos, to improve the cosmetic properties of the hair.

One problem common to all these products, however, is that a large proportion of the ionic polymers, as well as other trichocosmetic ingredients, are washed from the hair when the hair is rinsed with clear water. Thus, the potential cosmetic effect obtained from using such compositions is never realized to a full extent. Accordingly, numerous and repeated attempts have been made by the prior art to improve the deposition and retention on the hair of the above-mentioned ionic polymers and other water-insoluble trichocosmetic ingredients solubilized or dispersed in the compositions, by incorporating appropriate additives in the hair washing and rinsing preparations. Unfortunately, none of the solutions so far proposed has satisfied high consumer expectations in regard to the conditioning and structure-improving properties of shampoos and rinses.

DESCRIPTION OF THE INVENTION

It now has been found that aqueous-alcoholic compositions containing water-soluble ionic polymers and other trichocosmetic ingredients suitable for washing or rinsing hair show a considerably improved trichocosmetic effect when the compositions contain from about 0.1 to 20% by weight of a water-soluble salt of a saturated or unsaturated, aliphatic, alicyclic or aromatic di- or tri-carboxylic acid containing from 6 to 44 carbon atoms.

Ionic polymers suitable for use in the aqueous composition of the present invention are cationic, anionic and amphoteric or zwitter-ionic synthetic polymers or derivatives of naturally occurring polymers typically having molecular weights within the range of about 500 to 5,000,000 and having a sufficient number of ionic groups in, or attached to, the polymer chain that their salts are soluble in water. In the context of the present invention, soluble in water means that at least about 0.1% by weight of the salt of the ionic polymer is soluble in water at about 20° C.

Any of the wide variety of water-soluble cationic polymers known to be useful for treating hair are suitable for use in the present invention and include those polymers preferably having a molecular weight within the range of about 1,000–3,000,000, which contain either free or alkyl-substituted amino groups or quaternary ammonium groups in the main polymer chain or which carry secondary or tertiary amino groups or quaternary ammonium groups attached to the main polymer chain either directly or through intermediate members. The amino groups or quaternary ammonium groups also may be members of 5- or 6-membered ring systems, for example of morpholine, piperidine, piperazine or indazole rings. Several examples of suitable water-soluble cationic polymers are described, for example, in U.S. Pat. No. 4,240,450. In addition, many other water-soluble cationic polymers suitable for use in the present invention are well-known to those skilled in this technology from the technical literature. Particularly suitable are water-soluble homo- or copolymers containing units corresponding to the following general formula

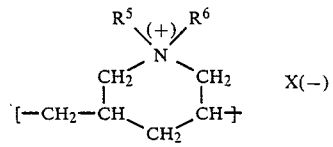

wherein $R^5$ and $R^6$ can represent a hydrogen atom, an alkyl group having from one to four carbon atoms or a hydroxyalkyl group having from two to four carbons atoms and $X^{(-)}$ is an anion such as a chloride, bromide, hydrogen sulfate, methoxy or ethoxy sulfate anion. The preparation of polymers such as these is described in U.S. Pat. No. 3,912,808. Products having this structure are commercially available and are sold, for example, under the trademarks Merquat® 100 (Merck & Co.) and Marquart® 550 (Quaternium 41).

Other Particularly suitable cationic polymers include, for example, cellulose ethers having a backbone of anhydroglucose units, each unit having from 1 to 3 substituents, which contain quaternary ammonium groups, attached to the polymer backbone through an ether oxygen. Polymers of this type are described, for example, in U.S. Pat. No. 3,472,840. One example of a commercial product having this structure is Polymer JR® 400 (Union Carbide Corporation).

Still other particularly suitable cationic polymers are, for example, quaternary polyvinyl pyrrolidone copolymers described in U.S. Pat. No. 3,910,862, which are available commercially, for example, under the trademark Gafquat® 734 and 755 (GAF Corp.), copolymers of adipic acid and dimethylaminohydroxypropyl diethylene triamine, described in U.S. Pat. No. 3,632,559, which are commercially available, for example, under the trademark Carataretine® F 4 and quaternary polymeric urea derivatives described in U.S. Pat. No. 4,157,388 which are commercially available, for example, under the trademark Mirapol® A15 (Miranol Chemical Co.).

Water-soluble anionic polymers suitable for use in the present invention include alkali metal, ammonium and alkanolammonium salts of polymers containing carboxylic acid or sulfonic acid groups, which are attached to a main polymer chain either directly or through intermediate members. Suitable polymers typically have a molecular weight of from about 500 to 5,000,000, preferably from about 1,000 to 3,000,000. These anionic polymers may be obtained, for example, by homopolymerization of acrylic or methacrylic acid; maleic acid or maleic acid anhydride; fumaric acid; itaconic acid, and the like or by copolymerization with non-ionic polymerizable monomers, such as, for example, acrylates or methacrylates; acrylamide or methacrylamide; vinyl esters, such as, for example, vinyl acetate or vinyl propionate; vinyl chloride; vinyl ethers, such as for example vinylmethyl ether; vinyl benzene; allyl and methallyl esters and the like. Particularly suitable anionic polymers are the carboxyl-group-containing polymers obtained by hydrolysis of poly-(ethylene/maleic acid anhydride) and poly-(methylvinylether/maleic acid anhydride) or obtained by hydrolysis of polyacrylates and polymethacrylates. Anionic copolymers prepared from methylvinyl ether and maleic acid anhydride are commercially available under the trademark Grantrez ® AN-Polymere.

Other particularly suitable anionic water-soluble polymers are poly-(aldehydocarboxylic acids) having an average molecular weight of from about 600 to 10,000 produced by oxidative homopolymerization of acrolein or by oxidative copolymerization of acrolein and acrylic acid. The salts of these poly-(aldehydocarboxylic acids) may be converted into the salts of poly-(hydroxycarboxylic acids) by disproportionation (after Cannizzaro) in the presence of alkalis, e.g., sodium hydroxide. This Cannizzaro reaction may be carried out in the presence of formaldehyde and may be accompanied by an aldol reaction to form poly-(hydroxycarboxylic acid) salts containing another hydroxymethyl group in the alpha-position to the carboxylate or hydroxymethyl groups formed from the aldehyde group. The production of these polymers is described, for example, in G.B. 1,296,412 and 1,296,413. Poly-(aldehydocarboxylic acids) and poly-(hydroxycarboxylic acids) such as these and their sodium salts are commercially available under the name POC (Degussa).

In the context of the present invention, water-soluble amphoteric polymers include polymers and copolymers wherein the polymer chain is composed both of units containing cationic groups and also units containing anionic groups, the cationic groups normally being free or alkyl-substituted amino groups and the anionic groups normally being carboxylate groups, sulfonate groups or sulfate ester groups. Also included are polymers and copolymers wherein the polymer chain is composed of units containing ampholytic groups. Suitable amphoteric polymers can be obtained, for example, by copolymerization of cationic, anionic and, optionally, nonionic monomers or by copolymerization of ampholytic and nonionic monomers. Zwitter-ionic polymers include polymers similar in structure to the amphoteric polymers, but containing quaternary ammonium groups instead of amino groups. Suitable polymers of this type preferably have a molecular weight between about 500 and 500,000.

Amphoteric and zwitter-ionic polymers suitable for use in the present invention may be obtained, for example, by the copolymerization of anionic monomers, such as acrylic acid, methacrylic acid, maleic acid and the like, with cationic monomers, such as dialkylaminoalkyl methacrylate or acrylate, dialkylaminoalkyl methacrylamide or acrylamide and the like as described for example in U.S. Pat. No. 3,836,537. A suitable commercial product of this type, an octyl-acrylamide/acrylate/butylaminoethyl methacrylate copolymer, is available under the trademark Amphomer ® (National Starch & Chemical Corp.). Other suitable zwitter-ionic polymers may be prepared by copolymerizing zwitter-ionic monomers, such as, for example, N-methacryloxyethyl-N,N-dimethylaminopropionate produced in accordance with U.S. Pat. No. 2,744,130, with nonionic monomers. Still other amphoteric and zwitter-ionic polymers for use in the present invention are described in G.B. 2,063,671 B.

The hair treatment compositions of the present invention suitable for washing or rinsing preferably contain the water-soluble ionic polymers described above as well as others which are apparent to those skilled in the art based on the present disclosure having the above-mentioned cationic, anionic amphoteric, or zwitter-ionic structure in a quantity of from about 0.1 to 5.0% by weight, preferably in an amount between about 0.2 and 2.0% by weight.

The second essential component of the aqueous composition of the present invention is a water soluble salt of a saturated or unsaturated, aliphatic, alicyclic or aromatic di- or tri-carboxylic acid containing from 6 to 44 carbon atoms. As was the case with the ionic polymer component, suitable di- and tri-carboxylic acids for use in the present invention are known to those skilled in the art in view of the present disclosure and various ones are commercially available. Preferred di- and tri-carboxylic acid salts for use in the present invention are those having two of the carboxyl (carboxylate) groups separated from each other by at least 3 carbon atoms.

For example, suitable aliphatic, alicyclic or aromatic di-carboxylic acids containing from 6 to 44 carbon atoms include adipic acid, azelaic acid, heptadecane-1,8-dicarboxylic acid, heptadecane-1,9-dicarboxylic acid, heptadecane-1,17-dicarboxylic acid, terephthalic acid, alkyl-substituted terephthalic acids containing up to 30 carbon atoms in the alkyl groups and mixtures of these di-carboxylic acids. Also suitable are adducts of unsaturated fatty acids, such as undecylenic acid, oleic acid, palmitoleic acid, linoleic acid, linolenic acid, conjugated polyunsaturated fatty acids or erucic acid, with monounsaturated carboxylic acids, such as acrylic or methacrylic acid, maleic acid or maleic acid anhydride or fumaric acid and the saturated acids formed by hydrogenation of any double bonds still present in the adducts. Among these adducts can be particularly mentioned the adduct of linoleic acid and acrylic acid which may be produced by the process described in U.S. Pat. No. 3,753,968, particularly the water soluble sodium, potassium and ammonium salts of this adduct. The Diels-Alder-like adduct mentioned therein, a $C_{21}$-di-carboxylic acid, consists of a mixture of 6-carboxyl-4-hexyl-2-cyclohexene-1-octanoic acid and 5-carboxy-4-hexyl-2-cyclohexene-1-octanoic acid and is described in detail in *J. Am. Oil Chem. Soc.* 52, (1975), pages 219–224. This mixture is commercially available under the trademark Westvaco Diacid ® 1550 (Westvaco Corp.).

Other suitable di-carboxylic acids are the unsaturated dimer acids which are obtained from unsaturated fatty acids by thermal addition, for example, from oleic acid and linoleic acid, and which are described, for example, in *J. Am. Oil Chem. Soc.* 39 (1962), pages 534–545, as well as the saturated di-carboxylic acids obtained therefrom by hydrogenation of any remaining double bonds. So-called dimer acids such as these are commercially available, for example, under the trademark Empol® 1010 (Unilever Emery Industries, Inc.).

Substituted succinic acids, for example, 2-alkyl and 2-alkenyl succinic acids, can be used in the present invention. The alkenyl succinic acids may be obtained from maleic acid anhydride and monoolefins, for example, by the process described in U.S. Pat. No. 2,411,215. The corresponding saturated alkyl succinic acids may be obtained from these adducts by hydrogenation of the double bond. However, it has been found that di- and tri-carboxylic acids, in which two of the carboxyl groups are separated from one another by at least three carbon atoms show greater activity.

The tri-carboxylic acid obtained by hydrolysis of the double bond addition adduct of undecylenic acid methyl ester and maleic acid anhydride, a 4-dodecene-1,2,4-tri-carboxylic acid can be used in the present invention and is described, for example, in *J. Am. Chem. Soc.* 68 (1946), pages 1373–1376. This compound may be converted into the saturated 1,2,4-dodecane tri-carboxylic acid by hydrogenation of the double bond. Other addition adducts suitable for use in the present invention are described in U.S. Pat. No. 2,188,882 and include the tri-carboxylic acids obtained by the addition reaction between maleic acid, maleic acid anhydride, maleic acid esters or fumaric acid, and unsaturated fatty acids and fatty acids esters, for example, oleic acid or linoleic acid, optionally followed by hydrolysis of the adducts.

The di- and tri-carboxylic acid component, including those described above as well as others which are apparent to those skilled in the art based on the present disclosure, is included in the hair washing or rinsing composition of the present invention in the form of a water-soluble salt, preferably the sodium salt, potassium salt, ammonium salt, or mono-, di- or trialkanolammonium salt containing from 2 to 4 carbon atoms in the alkanol group. The soluble di- or tri-carboxylic acid salt should be included in the composition in an amount of at least about 0.1% by weight. However, the solubility of these salts generally is much greater, so that quantities of up to about 20% by weight of these acid salts typically can be dissolved in the composition. Generally, these salts are included in the composition in an amount between about 1 to 10% by weight.

Particularly suitable salts for use in the present invention are the water soluble salts of 5(6)-carboxy-4-hexyl-2-cyclohexene-1-octanoic acid (Westvaco Diacid® 1550) and the salts of the isomeric carboxystearic acids, more especially the mixture of heptadecane-1,8-di-carboxylic acid and heptadecane-1,9-dicarboxylic acid. In addition to increasing the deposition and retention of ionic polymers on hair, these acid salts also have a particularly high solubilizing power (surfactant effect) for water-insoluble components, particularly cosmetic oil and fat components.

Particularly effective compositions useful for washing or rinsing hair according to the present invention are obtained when a quaternary ammonium compound also is included in the composition in a quantity of from about 0.1 to 5.0% by weight, preferably from about 0.5 to 2.5% by weight, in addition to the ionic polymer and the di- or tri-carboxylic acid salt. Preferably a quaternary ammonium compound corresponding to the following general formula is included in the composition

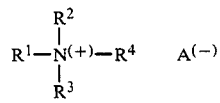

wherein $R^1$ is an alkyl, alkenyl or hydroxyalkyl group containing from 8 to 22 carbon atoms or is a $R^5$—CONH—$(CH_2)_x$— group, wherein $R^5$ is an alkyl group containing from 7 to 21 carbon atoms and x is an integer of from 2 to 4;

$R^2$ and $R^3$ represent a lower alkyl group having from 1 to 4 carbon atoms, a —$(C_nH_{2n}O)_y$—H group, in which n=2 or 3 and y is a number having a value of from 1 to 50;

$R^4$ is a benzyl group or is one of the groups identified as being suitable for $R^1$, $R^2$ or $R^3$; and $A^{(-)}$ is a chloride, bromide, methoxysulfate, ethoxysulfate, hydrogen sulfate or hydrogen phosphate anion.

Specific examples of quaternary ammonium compounds which may be used in the composition of the present invention are cetyl trimethylammonium chloride, stearyl dimethylbenzylammonium chloride, distearyl dimethylammonium chloride, acylamidopropyl dimethylethylammonium ethoxysulfate (a product of this latter type, in which the acyl group is derived from lanolin fatty acid, is commercially available under the trademark Lanoquat® 1756 (Emery Industries, Inc.) (Quaternium 33 and Ethyl Hexanol), acylamidopropyl trimethylammonium methoxysulfate (a product of this type in which the acyl group is derived from ricinoleic fatty acid is commercially available under the trademark Rewoquat® RTM50 (REWO). A wide variety of quaternary ammonium compounds suitable for use in this preferred embodiment are described, for example, in Hugo Janistyn "Handbuch der Kosmetika und Riechstoffe", Vol. III, 2nd Edition (1973), Dr. A. Huthig Verlag GmbH, Heidelberg, pages 419–420.

The hair-conditioning effect of the composition of the present invention is considerably enhanced by addition of the disclosed quaternary ammonium compound. Use of such quaternary ammonium compounds is particularly recommended for compositions intended for use as a hair rinse.

As noted above, the composition of the present invention, by virtue of the combination of a di- or tri-carboxylic acid salt, with an ionic polymer is not only effective in intensifying the effect of the trichocosmetically active ionic polymer on the hair fibers, it also promotes the deposition on the hair fibers of other water-insoluble components solubilized or dispersed in the composition. Such water-insoluble trichocosmetic components may include, for example, antidandruff agents, such as the zinc salts of 1-hydroxy-2-pyridine thione; ultraviolet filters such as, for example, N,N-dimethyl-4-aminobenzoic acid-2-ethylhexyl ester (Escalol® 507-Van Dyke & Co., Inc.); cosmetic oil and fat components, for example, fatty alcohols, such as cetyl alcohol and stearyl alcohol, fatty acid partial glycerides, such as stearic acid mono- and diglyceride, fatty acid fatty alcohol esters, such as for example decyl oleate, liquid branched alcohols, such as, for example, 2-octyl dodecanol or 2-hexyldecanol, fatty acid triglycerides, such as, for example, caprylic-capric acid triglyceride, fatty acid esters, such as, for example, isopropyl myristate, 2-ethylhexyl stearate, n-butylstearate and other standard cosmetic oils and fat components. These ingredients can be included in the composition at a concentration conventionally employed in shampoos and hair rinses. Compositions of the present invention useful as a hair rinse preferably contain from about 0.1 to 10% by weight of a water-insoluble cosmetic oil or fat component. The incorporation of these water-insoluble ingredients, such as the oil and fat components, in the hair washing and rinsing compositions of the present invention is considerably facilitated by the solubilizing effect of the di- and tri-carboxylic acid salts.

If it is desired to formulate a hair rinse containing a water-insoluble oil or fat component in solubilized form, the di- or tri-carboxylic acid salt should be used in an amount which yields a weight ratio of acid salt to oil or fat component of from about 2:1 to 50:1. Preferably the weight ratio of acid salt to oil or fat component is within the range of about 2:1 to 20:1. If, in a particular case, clear solubilization of the oil or fat component is not obtained in this way or if it is desired to use a smaller amount of the di- or tri-carboxylic acid salt, solubilization also may be aided by the addition of a low molecular weight alcohol (alkanol), for example, ethanol or isopropanol. A quantity of up to about 40% by weight of a low molecular weight alcohol is generally sufficient. The quantity of alcohol required for solubilization of an oil or fat in the composition of the present invention is always smaller than needed in compositions which do not contain a di- or tri-carboxylic acid salt.

Compositions according to the invention intended for use as shampoos additionally contain washing-active surfactants, preferably from about 1 to 25% by weight of an anionic, ampholytic, zwitter-ionic or nonionic surfactant. Such surfactants are commonly used in shampoos and require only a brief description to those skilled in this art.

Anionic surfactants suitable for use in shampoos of the present invention, for example, are conventionally employed synthetic sulfate or sulfonate surfactants. Suitable products of this type include, for example, the alkali salts, ammonium salts and alkanolammonium salts containing from 2 to 4 carbon atoms in the alkanol group of alkyl sulfates containing from 10 to 18 carbon atoms in the alkyl group, alkyl-(poly)-glycol ether sulfates containing from 10 to 10 carbon atoms in the alkyl group and from 1 to 12 glycol ether groups, alkane sulfonates containing from 10 to 18 carbon atoms, alkene and hydroxyalkane sulfonates of the type obtained by the sulfonation of alpha-olefins containing from 10 to 18 carbon atoms, fatty acid alkyl-olamide and fatty acid alkylolamide polyglycol ether sulfates, fatty acid monoglyceride sulfates, sulfosuccinic acid monoalkyl ester, acyl taurides and acyl isethionates containing from 10 to 18 carbon atoms in the acyl group.

Examples of ampholytic surfactants are N-($C_8$–$C_{18}$)-alkyl-$\beta$-aminopropionic acids or N-hydroxyethyl-N-cocosacylamidopropyl glycine. Examples of zwitter-ionic surfactants (betaine surfactants) are N-cocosalkyl-N,N-dimethyl glycine or N-cocosacylamidopropyl-N,N-dimethyl glycine.

Preferably, compositions of the present invention intended for washing hair contain nonionic surfactants. Suitable nonionic surfactants include, for example, adducts of ethylene oxide (from 6 to 20 moles) with $C_{12}$–$C_{18}$ fatty alcohols, with $C_{12}$–$C_{18}$ fatty acids, with alkylphenols containing from 8 to 12 carbon atoms in the alkyl group, with fatty acid alkylolamides, with fatty acid mono- and diglycerides, and with sorbitan fatty acid esters. Other suitable nonionic surfactants are the fatty acid mono- and diethanolamides and amine oxide surfactants. Suitable amine oxide surfactants include, for example, cocosalkyl dimethylamine oxide or cocosacylamidopropyl dimethylamine oxide. Other particularly suitable nonionic surfactants are the alkyl glucosides obtained from monosaccharides and monohydric $C_8$–$C_{25}$ alcohols in accordance with the process described in U.S. Pat. No. 3,598,865.

In addition to the essential water-soluble ionic polymer and di- or tri-carboxylic acid salt components and the preferred quaternary ammonium compound, water-insoluble cosmetic oil or fat component and washing-active surfactant optionally present, hair washing and rinsing compositions according to the present invention also may contain a wide variety of standard additives and formulation aids normally used in such compositions such as, for example, thickeners, e.g., of the nonionic water-soluble polymer type, such as polyvinyl pyrrolidone, hydroxyethyl cellulose or polyethylene glycols; opacifiers and pearlizers, e.g., ethylene glycol distearate or triethylene glycol distearate; pH stabilizers (buffers), e.g. alkali or ammonium phosphates or citrates; preservatives, e.g., formaldehyde, p-hydroxybenzoic acid esters or 2-methyl-4-isothiazolin-3-ones, as well as other trichocosmetic components such as, for example, anti-dandruff agents, sebostatic agents, vitamins, vegetable extracts, protein derivatives, dyes and perfumes. These optional ingredients can be used in the quantities conventionally employed in such compositions.

Hair rinses and shampoos prepared in accordance with the present invention are used in the same manner and frequency as commercially available preparations, e.g., daily, although due to the greater degree of deposition and retention of the trichocosmetic ingredients satisfactory results also can be obtained using such compositions weekly. Proper use of the present invention results in improved hair combability and set.

The following Examples are intended to illustrate further the present invention without limiting its scope which is defined by the appended claims.

EXAMPLES

The following commercial products are used in the following Formulation Examples:

| | |
|---|---|
| Lanoquat ® DES 50 | N—lanolin fatty acid amidopropyl-N,N—dimethyl-N—ethyl-ammonium ethoxysulfate, 50% in ethylhexane diol (Emery Industries, Inc.) |
| Westvaco Diacid ® 1550 | a mixture of 6-carboxy-4-hexyl-2-cyclohexane-1-octanoic acid with 5-carboxy-4-hexyl-2-cyclohexene-1-octanoic acid (Westvaco Corp.) |
| Polymer JR ® 400 | a cationic cellulose ether derivative containing quaternary ammonium groups (Union Carbide Corp.) |
| Gafquat ® 755 | a quaternary polyvinyl pyrrolidone copolymer, 20% by weight in water (GAF Corp., New York) |
| Escaldol ® 507 | 4-dimethylaminobenzoic acid-2-ethylhexyl ester, UV filter (Van Dyke & Co., Inc.) |
| Triton ® CG 110 | an alkyl glucose corresponding to the following general formula |

-continued

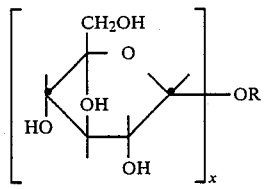

X = 1 — 5
R = $C_8/C_{10}$
alkyl group
(Rohm & Haas Co.)

| | |
|---|---|
| Rewoquat ® RTM 50 | ricinoleylamidopropyl trimethyl-ammonium methoxysulfate, 40% by weight in water (REWO) |
| Aminoxid WS ® 35 | cocosacyl-($C_{12}$-$C_{18}$)-amidopropyl-dimethylamine oxide, 35% by weight in water (TH. Goldschmidt) |
| POC HS 5060 ® | poly-(aldehydocarboxylic acid), average molecular weight approx. 4000, 40% by weight in water (DEGUSSA) |

Example 1

Hair Rinse Formulations

| | 1.1 | 1.2 |
|---|---|---|
| Cetyl trimethylammonium chloride | — | 1% by weight |
| Stearyl dimethylbenzyl-ammonium chloride | 1% by weight | — |
| Gafquat ® 755 | 4.0% by weight | 4% by weight |
| Sunflower Seed Oil | 0.5% by weight | — |
| Myristyl Alcohol | — | 1% by weight |
| Perfume Oil | — | 0.2% by weight |
| Westvaco Diacid ® 1550 | 1% by weight | 10% by weight |
| Triethanolamine | to pH 7.5 | to pH 7.7 |
| Water ad 100% by weight | ad 100% by weight | |
| Appearance at 20° C. | emulsion | clear |

Example 2

Demonstration of the increased deposition of solubilized active components on the hair Standardized human hair, which had been pretreated by bleaching and permanent waving once in either case was treated with a fixed (defined) quantity of hair rinse formulations 2.1, 2.2 and 2.3 identified in the table below and was thereafter thoroughly rinsed with clear water. Formulations 2.1 and 2.2 represent embodiments of the present invention while formulation 2.3 is a comparison example. After the hair treatment, the rinsing water was recombined with excess hair rinse and the quantity of Escalol ® 507 in the recovered mixture was determined by UV spectrometry. The quantity of Escalol ® 507 (mg/g hair) adsorbed onto the hair reported in the table was calculated by determining the difference between the total quantity of Escalol ® 507 used and the quantity in the recovered mixture and taking into account the total quantity by weight of hair used.

As shown below, the combination of the ionic polymer (Polymer JR ® 400) and di-carboxylic acid salt (Westvaco Diacid ® 1550) in the composition significantly improved the deposition and retention of the trichocosmetic UV filter (Escalol ® 507) relative to the composition (2.3) which did not contain this combination. Moreover, the further addition of a quaternary ammonium compound (Lanoquat ® DES 50) unexpectedly improved the performance of the composition in the presence of the ionic polymer and the di-carboxylic acid salt.

| | Test Formulation (Hair Rinses) | | |
|---|---|---|---|
| | 2.1 | 2.2 | 2.3 |
| Polymer JR ® 400 | 1% by weight | 1% by weight | — |
| Westvaco Diacid ® 1550 | 10% by weight | 10% by weight | 10% by weight |
| Lanoquat ® DES 50 | 5% by weight | — | 5% by weight |
| Escalol ® 507 | 5% by weight | 5% by weight | 5% by weight |
| Isopropanol | 25% by weight | 35% by weight | 25% by weight |
| Triethanolamine | to pH 7.5 | to pH 7.5 | to pH 7.5 |
| Water | ad 100% by weight | ad 100% by weight | ad 100% by weight |
| Quantity of Escalol 507 adsorbed (Mg/g hair) | 3.65 | 1.13 | 0.39 |

Example 3

Shampoo Formulation

| | |
|---|---|
| Triton ® CG 110 | 5% by weight |
| Aminoxid WS ® 35 | 3% by weight |
| Rewoquat ® RTM 50 | 1.2% by weight |
| POC HS 5060 ® | 5% by weight |
| Westvaco Diacid ® 550 | 7.5% by weight |
| Triethanolamine | to pH 7.5 |
| Perfume Oil | 0.2% by weight |
| Water | ad 100% by weight |

Although certain embodiments of the invention have been described in detail, it will be appreciated that other embodiments are contemplated along with modification of the disclosed features, as being within the scope of the invention. For example, although in certain cases di- or tri-carboxylic acids may exhibit sufficient water solubility in their free acid form, i.e., a water solubility of at least about 0.1% by weight, to permit their direct use in compositions of the present invention, the salts of such acids would exhibit even greater solubility characteristics and thus compositions of the present invention are best formulated using such acid salts.

We claim:

1. An aqueous or aqueous-alcoholic composition for washing or rinsing hair, comprising
    A. from about 0.1 to about 5.0% by weight of at least one water soluble ionic polymer, and
    B. from about 0.1 to about 20% by weight of a water-soluble salt of a saturated or unsaturated aliphatic, alicyclic or aromatic di- or tri-carboxylic acid containing from 6 to 44 carbon atoms wherein two of its carboxyl groups are separated from one another by at least 3 carbon atoms.

2. The composition of claim 1 wherein said di-carboxylic acid salt comprises an alkali, mono-, di- or tri-ethanolammonium salt of 5(6)-carboxyl-4-hexyl-2-cyclohexene-1-octanoic acid.

3. The composition of claim 1 which contains from about 1 to 10% by weight of said di- or tri-carboxylic acid salt.

4. The composition of claim 1 which also contains from about 0.1 to about 5.0% by weight of a quaternary ammonium compound corresponding to the following general formula

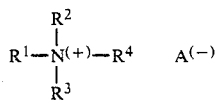

wherein $R^1$ is an alkyl, alkenyl or hydroxyalkyl group containing from 8 to 22 carbon atoms or a $R^5$—CONH—$(CH_2)_x$— group, wherein $R^5$ is an alkyl group containing from 7 to 21 carbon atoms and x is an integer of from 2 to 4;

$R^2$ and $R^3$ are alkyl groups having from 1 to 4 carbon atoms, or a —$(C_nH_{2n}O)_y$—H group, where n=2 or 3 and y is a number having a value of from 1 to 50;

$R^4$ is a benzyl group or is one of the groups identified as being suitable for $R^1$, $R^2$ or $R^3$; and $A^{(-)}$ is a chloride, bromide, methoxysulfate, ethoxysulfate, hydrogen sulfate or hydrogen phosphate anion.

5. The composition of claim 4 wherein said quaternary ammonium compound is present in an amount of from about 0.5 to about 2.5% by weight.

6. The composition of claim 1 suitable for use as a hair rinse, which also contains a water-insoluble cosmetic oil or fat component in an amount of from about 0.1 to about 10% by weight.

7. The composition of claim 6 wherein the weight ratio of the di-carboxylic acid salt or tri-carboxylic acid salt to the water-insoluble oil or fat component is within the range of about 2:1 to about 50:1.

8. The composition of claim 1 suitable for use as a shampoo, containing an anionic, ampholytic, zwitterionic or nonionic surfactant in an amount of from about 1 to about 25% by weight.

9. The composition of claim 7 wherein said weight ratio is in the range of from about 2:1 to about 20:1.

10. The composition of claim 8 wherein the surfactant is a nonionic surfactant.

11. The composition of claim 1 wherein component A is present in from about 0.2 to about 2.0% by weight.

12. The composition of claim 1 wherein component B is present in from about 1 to about 10% by weight.

* * * * *